United States Patent [19]

Bockow et al.

[11] Patent Number: 5,409,955
[45] Date of Patent: Apr. 25, 1995

[54] COMPOSITIONS AND METHODS FOR INHIBITING UTERINE CONTRACTILITY

[76] Inventors: Barry I. Bockow, 16122-8th Ave. SW., Suite D3, Seattle, Wash. 98166; Marc D. Erlitz, 12034 NE. 130th La. #101, Kirkland, Wash. 90834

[21] Appl. No.: 62,459

[22] Filed: May 13, 1993

[51] Int. Cl.$^6$ ................. A61K 31/235; A61K 31/225; A61K 31/20; A61K 31/19
[52] U.S. Cl. ................................ 514/560; 514/548; 514/568; 514/935; 514/533
[58] Field of Search ............... 514/533, 548, 560, 568, 514/935

[56] References Cited

U.S. PATENT DOCUMENTS 4,666,701  5/1987  Horrobin et al. .................. 424/10

OTHER PUBLICATIONS

Mindell, *Vitamin Bible*, Warner Books, Inc., 1991, pp. 26–29.
CA 101(13):104315b, Bogdashkin et al. (1984).
CA 110(9):69927q, Tang et al. (1988).
"Fish Oils in Pregnancy" *The Lancet* 339:1327–1328, 1992.
Calder and Greer, "Prostaglandins and the Biological Control of Cervical Function" *Reprod. Fertil. Dev.* 2:459–465, 1990.
Corey et al., "Docosahexaenoic acid is a strong inhibitor of prostaglandin but not leukotriene biosynthesis," *Proc. Natl. Acad. Sci. USA* 80:3581–3584, 1983.
Needleman et al., "Triene prostaglandins: Prostacyclin and thromboxane biosynthesis and unique biological properties," *Proc. Natl. Acad. Sci. USA* 76(2):944–948, 1979.
Sperling et al, "Effects of Dietary Supplementation with Marine Fish Oil in Leukocyte Lipid Mediator Generation and Function in Rheumatoid Arthritis," *Arthritis and Rheumatism* 30(9):988–997 (1987).
Kremer et al., "Dietary Fish Oil and Olive Oil Supplementation in Patients with Rheumatoid Arthritis," *Arthritis and Rheumatism* 33(6):810–820, 1990.
Lee et al., "Effect of Dietary Enrichment with Eicosapentaenoic and Docosahexaenoic Acids on In Vitro Neutrophil and Monocyte Leukotriene Generation and Neutrophil Function," *The New England Journal of Medicine* 312(19):1217–1224, 1985.
Furst and Paulus, "Aspirin and Other Nonsteroidal Anti-Inflammatory Drugs," *Arthritis and Allied Conditions-Textbook of Rheumatology* (10th ed.), Daniel McCarthy M.D., ed., Lea and Sebiger, pub., pp. 567–580, 1985.
Leaver et al., "The Effect of Dietary w3 and w6 Polyunsaturated Fatty Acids on Gestation, Parturition and Prostaglandin E2 in Intrauterine Tissues and the Kidney," *Prog. Lipid Research* 25:143–146, 1986.
Zuckerman et al., "Inhibition of Human Premature Labor by Indomethacin," *Journal of Obstetrics and Gynecology* 44(6):787–792, 1974.

*Primary Examiner*—Raymond Henley, III
*Assistant Examiner*—Kimberly R. Jordan
*Attorney, Agent, or Firm*—Seed & Berry

[57] ABSTRACT

There is disclosed a composition for inhibiting uterine contractility by topical or local administration. The composition contains an omega fatty acid in combination with a cyclo-oxygenase inhibitor. Preferred omega fatty acids include docosahexaenoic acid and eicosapentaenoic acid, and preferred cyclo-oxygenase inhibitors include acetylsalicylic acid and salicylic acid. The composition may further include pharmaceutically acceptable carriers or diluents, and may be locally applied via intracervical or intrauterine application, or may be topically applied to the skin of the lower abdomen.

10 Claims, No Drawings

COMPOSITIONS AND METHODS FOR INHIBITING UTERINE CONTRACTILITY

TECHNICAL FIELD

The present invention relates generally to compositions and methods for inhibiting uterine contractility and, more specifically, to compositions containing an omega fatty acid and a cyclo-oxygenase inhibitor and methods for topical and/or local administration of the same.

BACKGROUND OF THE INVENTION

The socioeconomic costs associated with health care affect all of society and effective treatments which reduce these costs are continuously sought and welcomed. One specific aspect of health care costs is the high cost associated with the care of premature infants. Premature infants are born of mothers whose pregnancy has not reached full term. Typically premature infants suffer from a variety of health problems due, at least in part, to their low birth weight. Premature infants require extensive medical care, the cost of which represents a significant burden on the health care system.

The premature birth of an infant results directly from the mother's premature labor. The onset of premature labor is characterized by uterine contractility. The contraction of the uterus is a response to a complex biological process in which a class of compounds known as prostaglandins play a controlling role. Prostaglandin synthesis occurs in tissues throughout the body, including the tissues of the uterus and cervix. In a pregnant woman, prostaglandin production increases during the term of pregnancy and culminates with a sharp increase at parturition. Because prostaglandins induce smooth muscle contraction, high uterine concentrations of these compounds at parturition initiate contractility and the onset of labor. This increase in uterine contractility is associated with a process known as "cervical ripening," which in turn progresses to cervical dilation. It is generally believed that the underlying mechanism associated with such changes in the cervix is similar to the inflammatory response which governs other biological processes. Among the changes that occur in the cervix are edema, increased vascular permeability with enzymatic changes and the resultant breakdown of collagen. Many of these changes are mediated by prostaglandins and leukotrienes, and cervical tissue levels of these inflammatory mediators are sharply increased at term.

The intermediacy and effectiveness of prostaglandins in the onset of labor is further evidenced by the long established use of prostaglandin E2 as a potent labor inducer. Conversely, effective inhibition of prostaglandin synthesis would lead to the suppression of uterine contractility and the delay of the onset of labor. Where labor is premature, the inhibition or prevention of prostaglandin synthesis may serve to avert the labor, and thereby avoid premature birth.

Prostaglandins are produced biosynthetically throughout the body. Prostaglandins are derived from enzymatic action on a common substrate, arachidonic acid. The first step in prostaglandin synthesis is the oxygenation of arachidonic acid by the enzyme cyclo-oxygenase. The oxygenated prostaglandin precursors are subject to further enzymatic processes which provide the various members of the prostaglandin family, including prostaglandin E2. Closely related in structure and function to the prostaglandins are a family of compounds known as leukotrienes. Leukotrienes are also derived from arachidonic acid metabolism, but through the lipoxygenase pathway. Like prostaglandins, leukotrienes enhance smooth muscle contraction and have also been implicated in uterine contractility.

Arachidonic acid is an essential fatty acid consisting of twenty carbon atoms and containing four carbon-carbon double bonds. By virtue of the position of carbon-carbon double bond at the methyl (omega) end of the hydrocarbon chain, it is classified as an omega-6 fatty acid. A closely related family of fatty acids are the omega-3 fatty acids. In addition to double bond position, omega-6 and omega-3 fatty acids may also be distinguished by their origins. The precursors to these fatty acids are derived from plants which are in turn further metabolized in animals to provide the long chain polyunsaturated acids. Omega-6 fatty acids may be found predominantly in land animals, while omega-3 fatty acids are abundant in fish.

The beneficial health effects of fish rich diets, such as overall cardiovascular health, have been attributed to omega-3 fatty acids. Corey et al., *Proc. Nat. Acad. Sci.* 80:3581–84 (1983). In addition, diets rich in omega-3 fatty acids have been associated with prolonged gestation and larger birth weights. Olsen et al., *Lancet* ii:3-67–69 (1986). In contrast, diets low in omega-3 fatty acids delivered earlier and smaller babies. Crawford et al., *Prog Lipid Res.* 25:249–54 (1986). The oral administration of omega-3 fatty acids has been shown to prolong gestation by delaying the onset of labor. Leaver et al., *Prog. Lipid Res.* 25: 143–46 (1986).

Oral administration of omega fatty acids, however, has limited effectiveness and suffers from several drawbacks. Fatty acids that are taken orally are subject to gastrointestinal absorption and metabolism. In order to achieve delivery of effective quantities of fatty acids to the uterus, large quantities must be administered. To compensate for the reduction of active compound reaching the targeted organ, increased dosages of fatty acids are required. In addition, oral administration of fatty acids is not tissue specific and the dosage is distributed throughout the body. Because these omega fatty acids affect biological processes beyond prostaglandin synthesis, side effects associated with oral administration have been observed. For example, omega fatty acids are known to interfere with normal platelet function, and oral administration generally results in the increased danger of bleeding. Rogers et al., *Atherosclerosis* 63:137–43 (1987). The effect of omega fatty acids on platelet function also adversely affects capillary fragility. The increased dosages necessary for effective reduction of uterine contraction serves to exacerbate the side effects due to interference with platelet function.

In general, agents which inhibit uterine contractility are known as "tocolytic" agents. Turbutaline sulphate is perhaps the most common tocolytic agent presently employed in obstetric practice (although not approved by the FDA for this indication), and is administered either orally or as a subcutaneous injection. However, serious adverse reactions may occur following administration of turbutaline sulphate to women in labor. In the mother, the potential adverse reactions include increased heart rate, transient hyperglycemia, hypokalemia, cardiac arrhythmia, pulmonary edema and myocardial ischemia. In addition, fetal heart rate and neonatal hypoglycemia may occur as a result of maternal administration (see Zurich et al., *Physicians Desk Reference*, 1993 Edition, Medical Economics Data, p. 1061).

Magnesium sulfate (i.e., epsom salts) has also been used to inhibit uterine contractility. Administration of this tocolytic agent is by continuous intravenous infusion. As with turbutaline sulphate, magnesium sulfate can produce undesirable side effects, including maternal cardiac and ECG changes, depression of neuromuscular function and somnolence. Moreover, this agent must be used with caution in patients with impaired renal function and, since magnesium sulfate crosses the placenta, it may result in adverse effects in the fetus.

While other tocolytic agents, such as indomethacin, have been used with limited success, reports of adverse fetal and neonatal effects (including oligohydramnios, premature closure of the ductus arteriosis and pulmonary hypertension) have limited their application. For example, in one series of experiments, postpartum hemorrhage was observed in 19% of mothers who received a single does of indomethacin (Keiss et al., *Intl. J Gynaecol. Obstet.* 44:787, 1974).

Accordingly, there is a need in the art for improved compositions and methods to inhibit uterine contractility and prevent premature labor. The present invention fulfills these objectives, and provides further related advantages.

SUMMARY OF THE INVENTION

Briefly stated, the present invention discloses methods and compositions for topical administration to effect a reduction of uterine contractility and prevent or inhibit premature birth in a pregnant patient. In one embodiment, a topical composition comprising an omega fatty acid and a cyclo-oxygenase inhibitor is disclosed. The composition contains therapeutically effective amounts of both an omega fatty acid and a cyclo-oxygenase inhibitor in combination with one or more acceptable carriers and/or diluents.

In a further embodiment, a method for reducing uterine contractility by administering a composition of this invention is disclosed. In this method, the composition is administered to a pregnant patient experiencing premature labor by local or topical application.

These and other aspects of this invention will become evident upon reference to the following detailed description.

DETAILED DESCRIPTION OF THE INVENTION

The present invention is generally directed to compositions which inhibit uterine contractility, as well as methods relating to the administration thereof. The compositions of the present invention contain both an omega fatty acid and a cyclo-oxygenase inhibitor. Although not intending to be limited to the following theory, it is believed that the compositions of the present invention effectively prevent the syntheses of the biochemicals responsible for uterine contraction, such as prostaglandins and leukotrienes, through interference with the cyclo-oxygenase and lipoxygenase pathways, respectively. For example, omega-3 fatty acids competitively inhibit the utilization of arachidonic acid in both cyclo-oxygenase and lipoxygenase pathways, and the cyclo-oxygenase inhibitor further inactivates the enzyme required for prostaglandin synthesis. The net effect of this combination renders the cyclo-oxygenase pathway and prostaglandin synthesis largely inoperative.

Fatty acids are a class of organic compounds that are characterized by a long hydrocarbon chain terminating with a carboxylic acid group. Fatty acids have a carboxyl end and a methyl (i.e., "omega") end. Omega-3 fatty acids are a family of unsaturated fatty acids where the unsaturated carbon most distant from the carboxyl group is the third carbon from the methyl terminus. In general, omega-3 fatty acids have the following general formula:

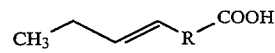

where R is a saturated or unsaturated, substituted or unsubstituted, branched or straight chain alkyl having from 1 to 20 carbon atoms. Preferably, R is an unsaturated straight chain alkyl having from 13 to 17 carbon atoms (i.e., an omega-3 fatty acid having from 18 to 22 total carbon atoms), and containing 2–6 carbon-carbon double bonds. In a particularly preferred embodiment, the omega-3 fatty acids of this invention contain 20 carbon atoms with 5 carbon-carbon double bonds, or 22 total carbon atoms with 6 total carbon-carbon double bonds, including (but not limited to) docosahexaenoic acid and eicosapentaenoic acid:

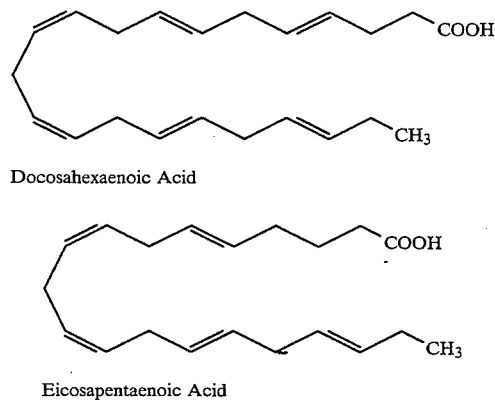

Docosahexaenoic Acid

Eicosapentaenoic Acid

Similarly, omega-6 fatty acids are a family of unsaturated fatty acids where the unsaturated carbon most distant from the carboxyl group is the sixth carbon from the methyl terminus. In general, omega-6 fatty acids have the following general formula:

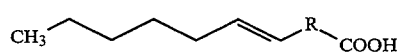

where R is a saturated or unsaturated, substituted or unsubstituted, branched or straight chain alkyl having from 1 to 20 carbon atoms.

While the omega fatty acids of this invention include both omega-3 and omega-6 fatty acids, omega-3 fatty acids are preferred.

The omega fatty acids of this invention are present in the composition in an amount sufficient to inhibit uterine contractility, in combination with the cyclo-oxygenase inhibitor, when topically or locally administered. A single omega fatty acid may be employed (such as a single omega-6 fatty acid or, preferably, a single omega-3 fatty acid), or a mixture of two or more different omega fatty acids may be used (such as a mixture of two or more omega-3 fatty acids, or a mixture of one or more omega-3 fatty acids and one or more omega-6 fatty acids).

Cyclo-oxygenase inhibitors of the present invention include any compound which effectively inhibits cyclo-oxygenase, including (but not limited to) acetylating and non-acetylating inhibitors. Cyclo-oxygenase inhibitors which acetylate cyclo-oxygenase (i.e, "acetylating inhibitors") include (but are not limited to) acetylsalicylic acid (aspirin) and salicylsalicylic acid, as well as salts thereof. Cyclo-oxygenase inhibitors which do not acetylate cyclo-oxygenase (i.e., "non-acetylating inhibitors") include (but are not limited to) salicylates, such as salicylic acid, trilisate, and disalcid, and salts thereof. Other cyclo-oxygenase inhibitors include naproxen, piroxicam, indomethacin, sulindac, meclofenamate, diflunisal, tolmetin, phenylbutazone, ibuprofen, fenoprofen, ketoprofen and nabumetome.

The cyclo-oxygenase inhibitors of the present invention are present in the composition in an amount sufficient to inhibit uterine contractility, in combination with the omega fatty acid, when topically or locally administered. A single cyclo-oxygenase inhibitor may be employed, or a mixture of two or more different cyclo-oxygenase inhibitors may be used.

The compositions of the present invention may also contain additional optional ingredients including, but not limited to, vitamin A. Vitamin A is believed to enhance adsorption of the composition. In addition, vitamin A appears to have a synergistic effect on the activity of the omega fatty acids of the present invention.

For purposes of administration, the compositions of the present invention may be formulated in any suitable manner for topical or local application, including (but not limited to) solutions, creams, oils, gels and vaginal suppositories. Such formulations contain effective amounts of both an omega fatty acid and a cyclo-oxygenase inhibitor, as well as one or more pharmaceutically acceptable carriers or diluents. More specifically, the formulations of the present invention may be topically or locally applied in the form of liquids, containing acceptable diluents such as saline and sterile water, or may be applied as lotions, creams or gels, containing acceptable diluents or carriers to impart the desired texture, consistency, viscosity and appearance. Such acceptable diluents and carriers are familiar to those skilled in the art and include (but are not limited to) emulsifying agents such as non-ionic ethoxylated and non-ethoxylated surfactants, fatty alcohols, fatty acids, organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, hydrophilic beeswax derivatives, hydrocarbon oils (such as palm oil, coconut oil, and mineral oil), cocoa butter waxes, silicon oils, pH balancers and cellulose derivatives. One skilled in this art may further formulate the omega fatty acid and cyclo-oxygenase inhibitor in an appropriate manner, and in accordance with accepted practices, such as those disclosed in *Remington's Pharmaceutical Sciences*, Gennaro, Ed., Mack Publishing Co., Easton, PA 1990 (which is incorporated herein by reference in its entirety).

As mentioned above, the omega fatty acid and cyclo-oxygenase inhibitor is present in the composition in an amount sufficient to inhibit uterine contraction when locally or topically applied. When formulated for local or topical application, the omega fatty acid is preferably present in an amount ranging from 1% to 90% by weight (based on the total weight of the formulation), more preferably from 10% to 80% by weight, and most preferably from 20% to 60% by weight. Similarly, the cyclo-oxygenase inhibitor is preferably present in an amount ranging from 0.1% to 20% by weight, more preferably from 1% to 10% by weight, and most preferably from 1% to 5% by weight.

The compositions of the present invention are administered by topical or local application (in contrast to systemic avenues, such as oral administration). For example, the compositions may be administered locally to the uterus via intravaginal or intracervical application (such application may also be made during laparotomy through the use of a laparoscope). Compositions administered in this manner will diffuse into the uterus. Alternatively, the compositions of this invention may be applied to the surface of the lower abdomen, and diffuse through the skin to the uterus. Topical administration in this manner may be enhanced through the use of ultrasound or iontophoresis, or a combination of the two.

The topical/local nature of the administration of the compositions of the present invention provide advantages over existing systemic (including oral) administration. In particular, topical and local administration provides for rapid and increased delivery of the active omega fatty acid and cyclo-oxygenase inhibitor to the uterus. The method of administration is therefore significantly more selective than oral administration and, as a result, smaller dosages of the active components are required. Furthermore, since the methods of administration of the present invention are specific to the uterus, the side effects of increased bleeding and capillary fragility associated with oral administration of omega fatty acids are also substantially reduced.

The following examples are provided for purposes of illustration, not by way of limitation.

EXAMPLES

Example 1

Compositions for Inhibition of Uterine Contractility

The following Formulations I and II are representative formulations containing the composition of the present invention.

|  | % by weight |
|---|---|
| Formulation I (cervical gel) | |
| Eicosapentaenoic acid | 40 |
| Docosahexaenoic acid | 5 |
| Salicylate | 3 |
| Vitamin A | 2 |
| Gel base | 50 |
| Formulation II (vaginal suppository) | |
| Eicosapentaenoic acid | 42 |
| Docosahexaenoic acid | 7 |
| Salicylate | 3 |
| Vitamin A | 5 |
| Suppository base | 43 |

Example 2

Administration of Composition for Inhibition of Uterine Contractility

The following example illustrates the administration of a representative composition of the present invention.

A woman, in the twenty-eighth week of pregnancy and experiencing premature labor, enters a hospital. After examination, the attending physician seeks to avoid premature delivery. The physician topically administers approximately 25 grams of Formulation I (Example 1) to the cervix every six hours over a period of one day (i.e., 4 applications over 24 hours). During this period, uterine contractions cease (as monitored with an external belt and sensor placed on the patient's abdomen). Formulation II (Example 1) is then administered in the form of a 50 gram vaginal suppository (replenished every 6–8 hours), and the patient is monitored for an additional 24 hours. After this period of time, all uterine contractions have ceased, and the patient is discharged subject to bed rest. A supply of vaginal suppositories of Formulation II is provided to the patient for application every 6–8 hours for an additional 3 days.

From the foregoing, it will be appreciated that, although specific embodiments of the invention have been described herein for purposes of illustration, various modifications may be made without departing from the spirit and scope of the invention. Accordingly, the invention is not limited except as by the appended claims.

We claim:

1. A method for inhibiting uterine contraction in a pregnant patient comprising topically or locally administering to the patient an effective amount of a composition comprising an omega fatty acid and a cyclo-oxygenase inhibitor.

2. The method of claim 1 wherein the composition is administered to the cervix in the form of a gel, cream or lotion.

3. The method of claim 1 wherein the composition is administered in the form of a vaginal suppository.

4. The method of claim 1 wherein the composition is administered to the surface of the lower abdomen.

5. The method of claim 1 wherein the omega-3 fatty acid of the composition has at least one of the following structures:

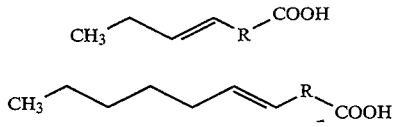

wherein R is a saturated or unsaturated, branched or straight chain alkyl having from 1 to 20 carbon atoms.

6. The method of claim 1 wherein the omega fatty acid is eicosapentaenoic acid.

7. The method of claim 1 wherein the omega fatty acid is docosahexaenoic acid.

8. The method of claim 1 wherein the cyclo-oxygenase inhibitor is an acetylating inhibitor selected from acetylsalicylic acid, salicylsalicylic acid, and salts thereof.

9. The method of claim 1 wherein the cyclo-oxygenase inhibitor is a non-acetylating inhibitor selected from salicylic acid trilisate, disalcid, and salts thereof.

10. The method of claim 1 wherein the cyclo-oxygenase inhibitor is selected from naproxen, piroxicam, indomethacin, sulindac, meclofenamate, diflunisal, tolmetin, phenylbutasone, ibuprofen, fenoprofen, ketoprofen and nabumetone.

* * * * *